United States Patent [19]
Bathellier et al.

[11] 3,966,804
[45] June 29, 1976

[54] METHOD OF PREPARATION OF HYDROXYLAMINE FORMIATE

[75] Inventors: Andre Bathellier, Sceaux; Michel Germain, Marcoussis, both of France

[73] Assignee: Commissariat a l'Energie Atomique, Paris, France

[22] Filed: May 20, 1974

[21] Appl. No.: 471,744

[30] Foreign Application Priority Data
May 18, 1973 France .............................. 73.18165

[52] U.S. Cl. ................................................ 260/542
[51] Int. Cl.[2] .................. C07C 51/52; C07C 135/00
[58] Field of Search ...................... 260/542, 540, 541

[56] References Cited
UNITED STATES PATENTS
3,336,375  8/1967  Jones .................................. 260/542

*Primary Examiner*—Vivian Garner
*Attorney, Agent, or Firm*—Sughrue, Rothwell, Mion, Zinn & Macpeak

[57] ABSTRACT

An anion exchange is carried out between an aqueous solution of a hydroxylamine salt and an organic solution of a formiate of an amine which is insoluble in water in accordance with the reaction:

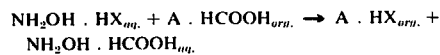

where
A represents the amine which is insoluble in water and
X represents the anion of the starting hydroxylamine salt.

4 Claims, No Drawings

METHOD OF PREPARATION OF HYDROXYLAMINE FORMIATE

This invention relates to a method of preparation of hydroxylamine formiate.

At the time of reprocessing of irradiated nuclear fuels by solvent extraction, selective stripping of plutonium from organic solvents calls for the use of reducing agents in order to convert the plutonium from the tetravalent state to the trivalent state. Among the reducing agents which are suitable for this purpose, hydroxylamine has an important advantage since it is readily destructible and does not contaminate the processing solutions. It can be employed especially in the form of hydroxylamine formiate which is of considerable interest in the case of selective stripping of plutonium by formic acid solutions, since the formic acid which is released into the solution at the time of reduction of the plutonium by the hydroxylamine formiate is favorable to the stripping process.

This invention relates to a method of preparation of hydroxylamine formiate from hydroxylamine salts such as hydroxylamine sulphate, hydrochloride or nitrate.

In accordance with the invention, the method of preparation of said hydroxylamine formiate consists in carrying out an anion exchange between an aqueous solution of a hydroxylamine salt and an organic solution of a formiate of an amine which is insoluble in water, in accordance with the reaction:

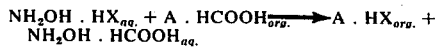

where

A represents the amine which is insoluble in water

X represents the anion of the starting hydroxylamine salt.

In accordance with a complementary feature of the invention, the starting hydroxylamine salt is selected from the group formed by hydroxylamine sulphate, nitrate and hydrochloride.

In accordance with another complementary feature, the amine which is insoluble in water is trilaurylamine.

The method is carried into effect in a multistage extractor of known type such as, for example, the type described in the article entitled "Mise en oeuvre industrielle de l'extraction liquide-liquide" ("Industrial application of liquid-liquid extraction") published in Bulletin d'Informations Scientifiques et Techniques No 184 of September, 1973. In this multistage extractor, the reacting solutions circulate in countercurrent flow, the amine being diluted in a hydrocarbon in order to improve the hydraulic operation of the apparatus.

The method in accordance with the invention is particularly advantageous since it is continuous. Moreover, the method entails the need for only a limited addition of reagents and makes it possible to prepare hydroxylamine formiate of high purity with a high yield by virtue of the fact that the hydroxylamine is not extracted by the organic solution of amine salt.

The following examples which are not given in any limiting sense illustrate the practical application of the method according to the invention.

EXAMPLE I

An aqueous solution of hydroxylamine hydrochloride $NH_2OH . HCl$ having a molar concentration of 2 is contacted in countercurrent flow within a 10-stage bank of mixer-settlers with ten times its volume of an organic solution having a concentration of 0.32 M of trilaurylamine and 0.77 M of total HCOOH. The organic diluent consists of tert-butylbenzene (Solgil 54 B manufactured by Societe Rhone-Progil) and the operation is performed at ordinary temperature. There is obtained at the outlet of the extractor an aqueous solution having a concentration of 1.7 M of hydroxylamine formiate $NH_2OH . HCOOH$ and $10^{-4}$ M of $Cl^-$ ions (26 ppm).

By slow evaporation of this solution, crystallized hydroxylamine formiate is obtained. The impurity of the hydroxylamine formiate obtained can be determined according to its residual content of $Cl^-$ ion which is 26 ppm. The hydroxylamine formiate conversion yield is 99.99 %.

Table I below gives the measured concentrations of the $Cl^-$ ion in each stage and each phase of the countercurrent flow process, the organic solution of trilaurylamine formiate being introduced into the first stage and the aqueous solution of hydroxylamine hydrochlorate being introduced into the last stage (No 10).

It is clearly apparent that the extraction of the chloride ion takes place steadily as the aqueous solution progresses from stage to stage and that, if necessary, a more complete elimination of said anion would be obtained by increasing the number of stages of the device.

EXAMPLE II

An aqueous solution of hydroxylamine nitrate $NH_2OH . HNO_3$ having a molar concentration of 2 is contacted in countercurrent flow within a 10-stage bank of mixer-settlers with ten times its volume of an organic solution having a concentration of 0.32 M of trilaurylamine and 0.77 M of total HCOOH. The organic diluent consists of tert-butylbenzene and the operation is carried out at ordinary temperature. There is obtained at the outlet of the extractor an aqueous solution having a concentration of 1.8 M of hydroxylamine formiate $NH_2OH . HCOOH$ and of $5 \times 10^{-4}$ M of $NO_3^-$ ion.

By slow evaporation of this solution, crystallized hyroxylamine formiate is obtained with a conversion yield of 99.95 % and a very high degree of purity as determined by its $NO_3^-$ ion content, namely 220 ppm.

Table II below gives the measured concentrations of the $NO_3^-$ ion in each stage and each phase of the countercurrent flow process, the organic solution of trilaurylamine formiate being introduced into the first stage and the aqueous solution of hydroxylamine nitrate being introduced into the last stage (No 10).

As in the first example, it is observed that the extraction of the nitrate ion takes place steadily from stage to stage as the aqueous solution progresses and that a more complete elimination of said anion can be obtained by increasing the number of stages of the device.

TABLE I

Distribution of the chloride ions in the countercurrent extraction process

| Stage | Moles of Cl organic phase | Moles of Cl aqueous phase |
|---|---|---|
| 1 | undetectable | $\epsilon$ |
| 2 | $\epsilon$ | $8 . 10^{-4}$ |
| 3 | $\epsilon$ | $8.5 . 10^{-3}$ |
| 4 | $\epsilon$ | $3.4 . 10^{-2}$ |
| 5 | $10^{-2}$ | $8.1 . 10^{-2}$ |

TABLE I-continued

Distribution of the chloride ions in the countercurrent extraction process

| Stage | Moles of Cl⁻ organic phase | Moles of Cl⁻ aqueous phase |
|---|---|---|
| 6 | — | 0.16 |
| 7 | $3.5 \cdot 10^{-2}$ | 0.17 |
| 8 | $5 \cdot 10^{-2}$ | 0.44 |
| 9 | $9.2 \cdot 10^{-2}$ | 0.72 |
| 10 | 0.17 | 1.23 |

TABLE II

Distribution of the nitrate ions in the countercurrent extraction process

| Stage | Moles of $NO_3^-$ organic phase | Moles of $NO_3^-$ aqueous phase |
|---|---|---|
| 1 | undetectable | $\epsilon$ |
| 2 | $\epsilon$ | $\epsilon$ |
| 3 | $\epsilon$ | $3 \cdot 10^{-3}$ |
| 4 | $\epsilon$ | $7 \cdot 10^{-3}$ |
| 5 | $2 \cdot 10^{-3}$ | $1.7 \cdot 10^{-2}$ |
| 6 | $4.4 \cdot 10^{-3}$ | $4 \cdot 10^{-2}$ |
| 7 | $10^{-2}$ | $10^{-1}$ |
| 8 | $2.6 \cdot 10^{-2}$ | $2.4 \cdot 10^{-1}$ |
| 9 | $6 \cdot 10^{-2}$ | $5.5 \cdot 10^{-1}$ |
| 10 | $1.5 \cdot 10^{-1}$ | 1.3 |

What we claim is:

1. A method of preparation of hydroxylamine formiate consisting of conducting an anion exchange by continuous extraction of anions between an aqueous solution of a hydroxylamine salt selected from the group consisting of hydroxylamine sulphate, hydroxylamine hydrochloride and hydroxylamine nitrate, and an organic solution of trilaurylamine formiate in accordance with the reaction:

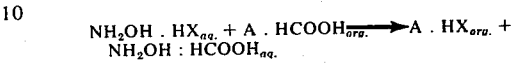

where A represents the trilaurylamine and X represents the anion of the starting hydroxylamine salt, so as to obtain an aqueous solution of hydroxylamine salt.

2. A method according to claim 1, wherein the continuous extraction is performed by contacting said organic and aqueous solution in countercurrent flow within a multistage extractor.

3. A method according to claim 2, wherein the volume ratio of organic solution to aqueous solution is about 10:1, and wherein the molar concentration of said aqueous solution of hydroxylamine salt is about 2.

4. A method according to claim 2, wherein said trilaurylamine has a concentration of 0.32M.

* * * * *